United States Patent
Uebayashi et al.

(10) Patent No.: US 9,050,058 B2
(45) Date of Patent: Jun. 9, 2015

(54) X-RAY DIAGNOSTIC SYSTEM AND X-RAY DIAGNOSTIC METHOD

(71) Applicants: Kabushiki Kaisha Toshiba, Tokyo (JP); Toshiba Medical Systems Corporation, Otawara-shi (JP)

(72) Inventors: Yoshinori Uebayashi, Utsunomiya (JP); Satoru Nakanishi, Utsunomiya (JP)

(73) Assignees: Kabushiki Kaisha Toshiba, Tokyo (JP); Toshiba Medical Systems Corporation, Otawara-shi (JO)

( * ) Notice: Subject to any disclaimer, the term of this patent is extended or adjusted under 35 U.S.C. 154(b) by 187 days.

(21) Appl. No.: 13/760,539

(22) Filed: Feb. 6, 2013

(65) Prior Publication Data
US 2013/0208853 A1 Aug. 15, 2013

(30) Foreign Application Priority Data
Feb. 9, 2012 (JP) ................................. 2012-025848

(51) Int. Cl.
*A61B 6/00* (2006.01)
*A61B 6/03* (2006.01)

(52) U.S. Cl.
CPC . *A61B 6/54* (2013.01); *A61B 6/032* (2013.01); *A61B 6/488* (2013.01); *A61B 6/542* (2013.01); *A61B 6/545* (2013.01)

(58) Field of Classification Search
CPC ........ A61B 6/032; A61B 6/542; A61B 6/545; G01N 23/046
USPC ................................ 378/4–20; 382/128–131
See application file for complete search history.

(56) References Cited

U.S. PATENT DOCUMENTS

2005/0185760 A1 * 8/2005 Suzuki ......................... 378/109

FOREIGN PATENT DOCUMENTS

| JP | 2001-218761 | 8/2001 |
| JP | 2004-325183 | 11/2004 |
| JP | 2009-50531 | 3/2009 |
| JP | 2011-120725 | 6/2011 |

* cited by examiner

*Primary Examiner* — Courtney Thomas
(74) *Attorney, Agent, or Firm* — Oblon, McClelland, Maier & Neustadt, L.L.P.

(57) ABSTRACT

An X-ray diagnostic system according to an embodiment includes: an X-ray tube for radiating an X-ray to the subject on the basis of a tube current for taking a scanogram of a subject; an X-ray detector for detecting the X-ray radiated by the X-ray tube and transmitted through the subject; a data collector for collecting X-ray dose distribution data, which shows the dose distribution of the X-ray; an image processor for creating the scanogram from the X-ray dose distribution data; a genuine data generator for generating genuine data showing the dose distribution of the X-ray, from the scanogram; a threshold value setting section for setting a threshold value for the genuine data; and a tube current adjustor for adjusting a tube current for taking a tomographic image of the subject in accordance with a comparison between the X-ray dose in the genuine data and the threshold value.

16 Claims, 6 Drawing Sheets

X-RAY DIAGNOSTIC SYSTEM AND X-RAY DIAGNOSTIC METHOD

CROSS-REFERENCE TO THE RELATED APPLICATION

This application is based on and claims the benefit of priority from Japanese Patent Applications No. 2012-025848, filed on Feb. 9, 2012; the entire contents of which are incorporated herein by reference.

FIELD

Embodiments described herein relate generally to an X-ray diagnostic system and an X-ray diagnostic method.

BACKGROUND

An X-ray diagnostic system radiates an X-ray to a subject such as a patient, detects the X-ray transmitted through the subject, and collects the dose distribution data of the detected X-ray (X-ray transmission data) by use of a data collector. Thereafter, the X-ray diagnostic system performs a reconstruction process on the dose distribution data, and creates a slice image (tomographic image) of the subject. An exemplary one developed as this X-ray diagnostic system is an X-ray CT system (X-ray computed tomography system) configured to take radiographs of a subject with an X-ray radiator and an X-ray detector opposed to each other with the subject therebetween and rotated around the body axis of the subject.

The X-ray diagnostic system like this is configured to collect scanograms (positioning images) by taking radiographs without rotating the X-ray radiator or the X-ray detector for the purpose of setting a scanning range before radiographing such as multi-slice scanning or helical scanning. Among X-ray diagnostic systems of this type, there has already been a product which includes auto exposure control (AEC) configured to convert the thickness of each bodily part into a water equivalent thickness by use of the scanograms, and to determine a tube current value (mA) on the basis of a specified SD (Standard Deviation).

The AEC automatically calculates, from the scanograms, an X-ray dose suitable for the bodily thickness of each part of the subject, and thereafter finely controls the x-ray dose, namely a tube current, for each rotation of the X-ray radiator and the X-ray detector. This realizes a reduction in radiation exposure by inhibiting unnecessary radiation exposure while maintaining high-quality images.

Although, however, the above-described technology adjusts the tube current in accordance with the size (bodily thickness) of the subject, the tube current determined through the adjustment is merely adjusted within a limited range of a maximum value and a minimum value determined by the system capacities. This is likely to cause artifacts such as an overflow artifact (an artifact appearing on a reconstruction image due to an excess over the maximum value of a count which can be handled in the data collector) and an artifact dark-band artifact (an artifact appearing on a reconstruction image due to a shortage in an X-ray dose, namely a shortage in a raw data count). This artifact degrades the image quality of X-ray images such as tomographic images.

DETAILED DESCRIPTION

According to one embodiment, an X-ray diagnostic system includes: a tube current setting section for setting a tube current for taking a scanogram of a subject; an X-ray tube for radiating an X-ray to the subject on the basis of the tube current for taking the scanogram, the tube current set by the tube current setting section; an X-ray detector for detecting the X-ray radiated by the X-ray tube and transmitted through the subject; a data collector for collecting X-ray dose distribution data, which shows the distribution of the X-ray detected by the X-ray detector; an image processor for creating the scanogram from the X-ray dose distribution data collected by the data collector; a genuine data generator for generating genuine data showing the dose distribution of the X-ray detected by the X-ray detector, from the scanogram created by the image processor, or from raw data produced in the process of creating the scanogram by the image processor; a threshold value setting section for setting a threshold value for the genuine data generated by the genuine data generator; and a tube current adjustor for adjusting a tube current for taking a tomographic image of the subject in accordance with a comparison between the X-ray dose in the genuine data generated by the genuine data generator and the threshold value set by the threshold value setting section.

According to another embodiment, an X-ray diagnostic method includes the steps of: setting a tube current for taking a scanogram of a subject; radiating an X-ray onto the subject on the basis of the set tube current for taking the scanogram; detecting the X-ray transmitted through the subject; collecting X-ray dose distribution data, which shows the dose distribution of the detected X-ray; creating the scanogram from the collected X-ray dose distribution data; generating genuine data showing the dose distribution of the X-ray from the created scanogram, or from raw data produced in the process of creating the scanogram; setting a threshold value for the generated genuine data; and adjusting a tube current for taking a tomographic image of the subject in accordance with a comparison between the X-ray dose in the generated genuine data and the set threshold value.

An embodiment is described with reference to the drawings.

Figure 1:
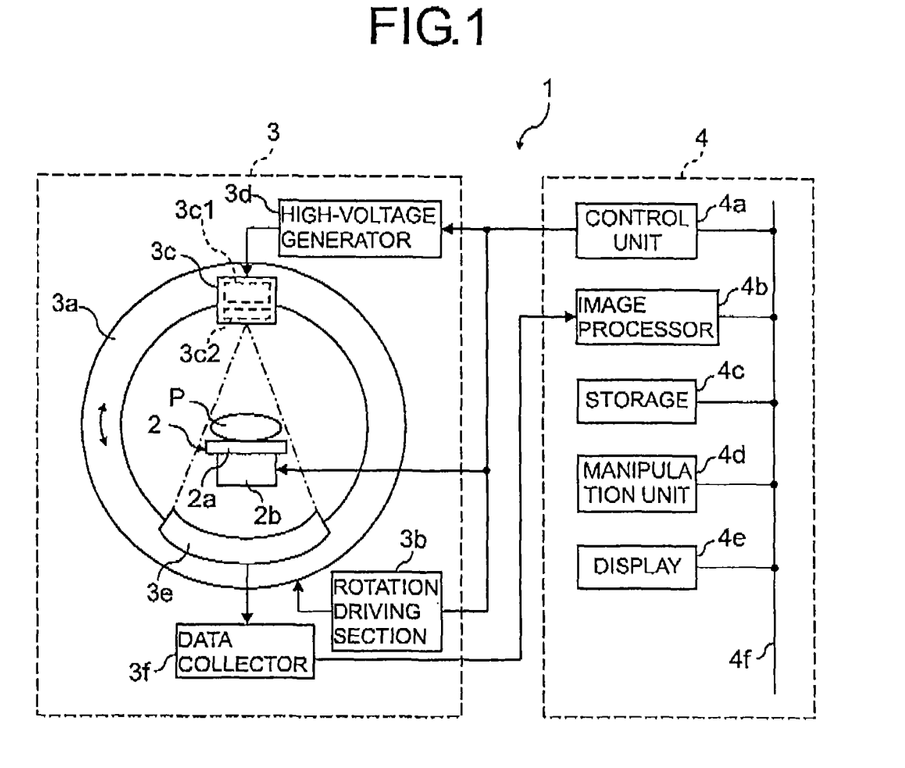
FIG. 1 is a diagram showing a schematic configuration of an X-ray diagnostic system of an embodiment.

As shown in FIG. 1, an X-ray diagnostic system 1 of the embodiment includes: a bed 2 on which a subject P such as a patient lies; an image taking unit 3 for taking an image of the subject P on the bed 2; and a controller 4 for controlling the bed 2 and the image taking unit 3. An X-ray CT system (X-ray computed tomography system), for example, is cited as the X-ray diagnostic system 1.

The bed 2 includes: a rectangular top board 2a on which to place the subject P; and a top board driving section 2b for supporting the top board 2a, and for moving the top board 2a in the horizontal direction and in the vertical direction (an ascent-and-descent direction). The top board driving section 2b includes: a movement mechanism for moving the top board 2a; and a driving source for supplying driving force for the movement. The bed 2 moves the subject P on the top board 2a to a desired position by: moving the top board 2a by the top board driving section 2b to a desired height; and further moving the top board 2a in the horizontal direction.

The image taking unit 3 includes: a rotary body 3a rotatably provided in a CT gantry serving as a housing; a rotation driving section 3b for rotating the rotary body 3a; an X-ray radiator 3c for radiating an X-ray; a high-voltage generator 3d for supplying a high voltage to the X-ray radiator 3c; an X-ray detector 3e for detecting the X-ray transmitted through the subject P on the top board 2a; and a data collector 3f for collecting the X-ray detected by the X-ray detector 3e as X-ray dose distribution data (X-ray transmission data).

The rotary body 3a is an annular rotary frame which rotates while supporting the X-ray radiator 3c, the X-ray detector 3e and the like. The rotary body 3a is provided with the X-ray radiator 3c and the X-ray detector 3e. The X-ray radiator 3c and the X-ray detector 3e rotates around the body axis of the subject P, away from the subject P, with the subject P on the top board 2a interposed in between.

The rotation driving section 3b is provided in the CT gantry of the image taking unit 3. The rotation driving section 3b rotationally drives the rotary body 3a in accordance with the control by the controller 4. For example, the rotation driving section 3b rotates the rotary body 3a at a predetermined rotary speed in one direction on the basis of a control signal sent from the controller 4.

The X-ray radiator 3c includes: an X-ray tube 3c1 for emitting the X-ray; and a diaphragm device 3c2 including a collimator, and making the X-ray emitted from the X-ray tube 3c1 converge. The X-ray radiator 3c is fixed to the rotary body 3a. The X-ray radiator 3c radiates the X-ray shaped like a fan beam having a cone angle to the subject P on the top board 2a, for example like a pyramid, by making the X-ray tube 3c1 emit the X-ray; and making the X-ray converge by use of the diaphragm device 3c2.

In this respect, various types of diaphragm devices may be used as the diaphragm device 3c2. For example, a diaphragm device may be used in which: two X-ray shielding plates made of lead are moved in directions in which the two X-ray shielding plates are brought close to and away from each other; and the size of a space formed between the X-ray shielding plates is changed appropriately. The space constitutes a passage area of the X-ray, while an area other than the space constitutes a shielding area which shields against the X-ray. The radiation field (radiation range) of the X-ray can be adjusted by the diaphragm device 3c2 like this.

The high-voltage generator 3d is provided in the CT gantry of the image taking unit 3 and is configured to generate the high-voltage to be supplied to the X-ray tube 3c1 of the X-ray radiator 3c. The high-voltage generator 3d boosts and rectifies a voltage given from the controller 4, and supplies the resultant voltage to the X-ray tub 3c1. Incidentally, the controller 4 controls various conditions for a voltage waveform to be given to the high-voltage generator 3d, namely its amplitude and pulse width, in order to make the X-ray tube 3c1 generate the desired X-ray.

The X-ray detector 3e is fixed to the rotary body 3a while opposed to the X-ray radiator 3c. The X-ray detector 3e converts the X-ray transmitted through the subject P on the top board 2a, into an electric signal, and sends the electric signal to the data collector 3f. The X-ray detector 3e is a multiseriate and multichannel X-ray detector, and includes X-ray detecting elements for detecting the X-ray which are arrayed in a matrix form. Incidentally, channel columns are multiple columns in which multiple (for example, approximately hundreds to thousands of) X-ray detecting elements are arrayed in a channel direction (a direction along the circumference of the body axis of the subject P), and the multiple (for example, 16, 64, etc.) channel columns are arrayed in a row direction (a direction along the body axis of the subject P).

In this respect, an X-ray detector of a photon counting type, which is configured to count photons, is used as the X-ray detector 3e. However, the X-ray detector 3e is not limited to this type. The X-ray detector 3e may be that (for example, a plane detector) of a direct conversion type which is configured to directly convert an X-ray into an electric signal, or that of an indirect conversion type which is configured to convert an X-ray into optical information, and thereafter convert the optical information into an electric signal.

The data collector 3f is provided in the CT gantry of the image taking unit 3. The data collector 3f converts the electric signal sent from the X-ray detector 3e into a digital signal, collects the X-ray transmission data (the X-ray dose distribution data), which is digital data, and sends the X-ray transmission data to the controller 4.

The controller 4 includes: a control unit 4a for controlling the components; an image processor 4b for performing various kinds of image processing on the X-ray transmission data; a storage 4c for storing various programs and various sets of data; and a manipulation unit 4d to which the user applies input manipulation; and a display 4e for displaying images. The control unit 4a, the image processor 4b, the storage 4c, the manipulation unit 4d and the display 4e are electrically connected together through a bus line 4f.

The control unit 4a controls various components, such as the top board driving section 2b of the bed 2, and the rotation driving section 3b and the high-voltage generator 3d of the image taking unit 3, on the basis of the various programs and the various sets of data which are stored in the storage 4c. In addition, the control unit 4a controls the diaphragm device 3c2 of the X-ray radiator 3c. Furthermore, the control unit 4a performs display control for displaying various images, such as X-ray images, on the display 4e. A CPU (Central Processing Unit) or the like, for example, may be used as the control unit 4a.

The image processor 4b performs image processing such as a pre-process for treating the X-ray transmission data sent from the data collector 3f as projection data; an image reconstruction process for performing image reconstruction on the projection data; and a scanogram creating process for creating a scanogram. An array processor or the like, for example, may be used as the image processor 4b.

The storage 4c is a storage device for storing the various programs and the various sets of data. For example, as part of the various sets of data, the scanogram (positioning image) and a slice image (a tomographic image) are stored in the storage 4c. A ROM (Read Only Memory), a RAM (Random Access Memory), a hard disc (a magnetic disc device), a flash memory (a semiconductor disc memory) and the like may be used as the storage 4c.

The manipulation unit 4d is an input section for receiving input manipulation by the user. For example, the manipulation unit 4d receives various kinds of manipulation such as an instruction for taking an image, displaying an image, switching images, and setting various items. Input devices, such as a key board, a mouse and a lever, may be used as the manipulation unit 4d.

The display 4e is a display device for displaying various images such as the scanogram and tomographic image of the subject P, as well as images for the manipulation. A liquid crystal display, a CRT (cathode-ray tube) or the like, for example, may be used as the display 4e.

In this respect, the above-described X-ray diagnostic system 1 has various image taking modes, for example, a scanogram taking mode for taking the scanogram, and tomographic image taking modes for taking the slice image. A normal multi-slice scanning mode (for normal CT), a helical scanning mode (for helical CT), a volumetric scanning mode (for volumetric CT) and the like, for example, can be cited as the tomographic image modes.

The scanogram taking mode is that which is configured to take a scanogram for positioning and setting a scanning range (an image taking range) prior to radiographing in the tomographic image taking mode. In scan planning, a scanogram is taken beforehand; the scanogram is displayed by the display 4e; and the operator checks the scanogram and sets a scanning range by applying input manipulation to the manipulation unit 4d.

In the scanogram taking, the X-ray radiator 3c and the X-ray detector 3e are fixed to respective predetermined positions, that is to say, at a predetermined view angle (for example, 0 degree or 90 degrees); the top board 2a of the bed 2 is moved to a predetermined position in the direction of the body axis of the subject P; the X-ray is radiated by the X-ray radiator 3c; the X-ray transmitted through the subject P on the top board 2a is detected by the X-ray detector 3e; and the X-ray transmission data is collected. Thereafter, the scanogram is created by processing the collected X-ray transmission data by the image processor 4b; and the created scanogram is stored in the storage 4c, and is displayed on the display 4e.

On the other hand, in the tomographic image taking, the X-ray radiator 3c and the X-ray detector 3e are rotated; the X-ray is radiated from the X-ray radiator 3c while moving the top board 2a of the bed 2 in the direction of the body axis of the subject P; the X-ray transmitted through the subject P on the top board 2a is detected by the X-ray detector 3e; and the X-ray transmission data is collected. Thereafter, the tomographic image is created by processing the collected X-ray transmission data by the image processor 4b; and the created tomographic image is stored in the storage 4c, and is displayed on the display 4e.

In this respect, detailed descriptions will be provided for the above-described control unit 4a.

Figure 2:
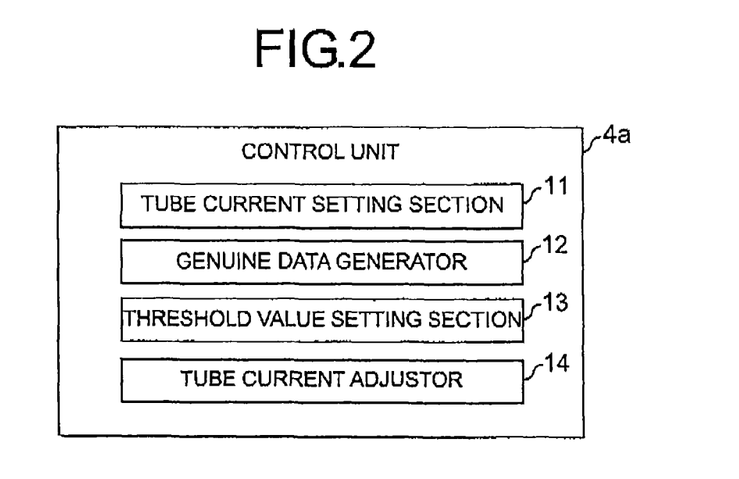
FIG. 2 is a diagram showing a schematic configuration of a controller included in the X-ray diagnostic system.

As shown in FIG. 2, the control unit 4a includes: a tube current setting section 11 for setting a tube current for taking the scanogram of a subject P; a genuine data generator 12 for obtaining raw data from the scanogram, and generating genuine data (the X-ray dose distribution data which shows the dose distribution of the X-ray actually received by the X-ray detector 3e when taking the scanogram) from the raw data; a threshold value setting section 13 for setting a threshold value for the genuine data; and a tube current adjustor 14 for adjusting a tube current for taking the tomographic image of the subject P in accordance with a comparison between the X-ray dose in the genuine data and the threshold value.

The tube current setting section 11, the genuine data generator 12, the threshold value setting section 13 and the tube current adjustor 14 may be formed from hardware including electric circuits, or from software including programs for executing these functions. Otherwise, the tube current setting section 11, the genuine data generator 12, the threshold value setting section 13 and the tube current adjustor 14 may be formed from a combination of both hardware and software.

Next, descriptions will be provided for the process of adjusting the tube current for taking the tomographic image, which is performed by the above-described X-ray diagnostic system 1. On the basis of various kinds of programs and various sets of data, the control unit 4a performs the tube current adjustment process for taking the tomographic image by use of various components such as the tube current setting section 11, the genuine data generator 12, the threshold setting section 13 and the tube current adjustor 14.

Figure 3:
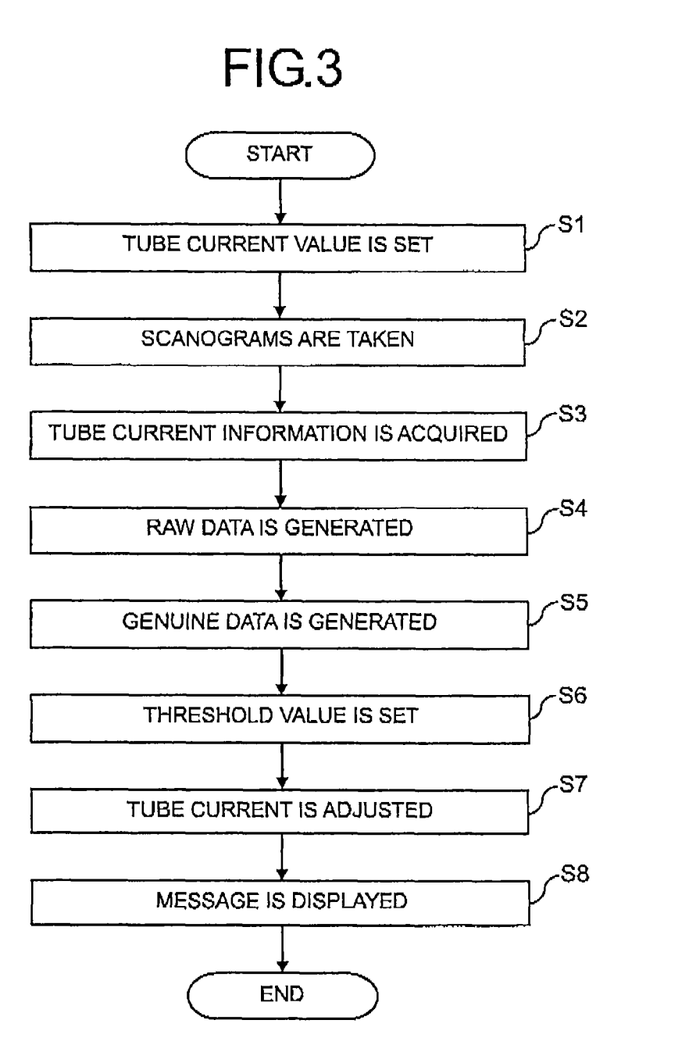
FIG. 3 is a flowchart showing the sequence of a process of adjusting a tube current for taking a tomographic image, which is performed by the X-ray diagnostic system.

As shown in FIG. 3, a tube current is set in response to the user's input manipulation on the manipulation unit 4d (step 1). In step S1, the tube current value is automatically set by auto exposure control (AEC) in a case where, for example, the user sets a standard deviation (SD) through his/her input manipulation on the manipulation unit 4d. Otherwise, in a case where the user directly inputs a tube current through his/her manipulation on the manipulation unit 4d, the inputted value is set as the tube current value. Once the tube current value is set as described above, tube current information on the set tube current value is stored in the storage 4c.

After the process in step S1, scanograms are taken on the basis of the set tube current value (step S2). In step S2, the scanograms are taken in positions at view angles of 0 degree (for a plane position) and 90 degrees (for a lateral surface position), respectively. The scanograms thus taken are stored in the storage 4c. In this regard, the radiation field is set largest (for example, with 512 pixels×512 pixels).

Figure 4:
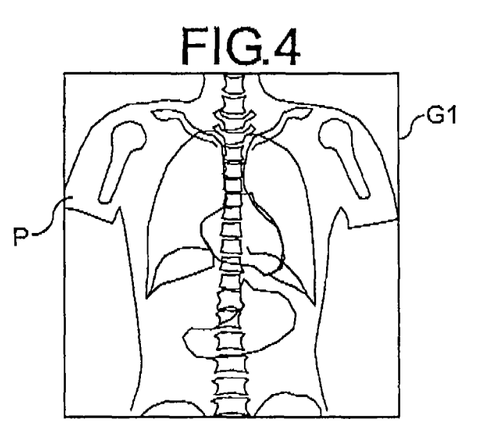
FIG. 4 is an explanatory drawing for explaining a plan scanogram (a scanogram in an AP direction).
Figure 5:
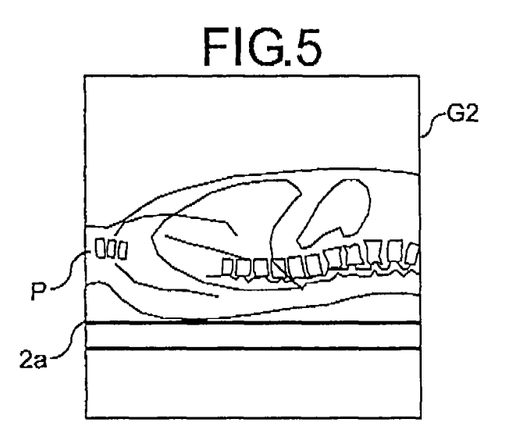
FIG. 5 is an explanatory drawing for explaining a side scanogram (a scanogram in an LR direction).

When a scanogram is taken in the plane position at the view angle of 0 degree, an X-ray is radiated to the top surface of the subject P on the top board 2a, and the X-ray transmitted through the subject P is detected. Accordingly, a plane image G1 is taken as a scanogram representing the plane of the subject P, as shown in FIG. 4. This plane image G1 is termed as a scanogram in the AP direction (the anterior-posterior direction). When a scanogram is taken in the lateral surface position at the view angle of 90 degrees, an X-ray is radiated to a lateral surface of the subject P on the top board 2a, and the X-ray transmitted through the subject P is detected. Accordingly, a lateral surface image G2 is taken as a scanogram representing the lateral surface of the subject P, as shown in FIG. 5. This lateral surface image G2 is termed as a scanogram in the LR direction (the left-right direction).

Figure 6:
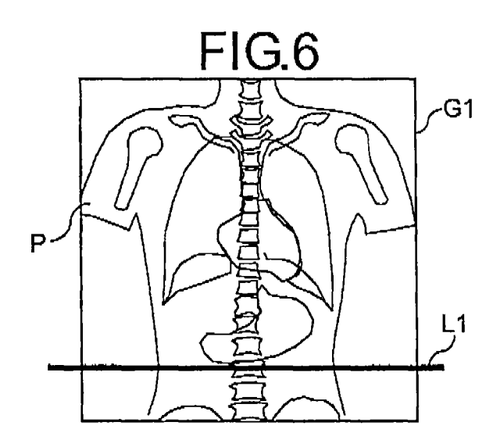
FIG. 6 is an explanatory drawing for explaining a line in the plan scanogram.

Returning to FIG. 3, after the process in step S2, the tube current information is acquired by being retrieved from the storage 4c (step S3). Thereafter, raw data is generated from at least one of the scanograms (step S4). In step S4, as shown in FIG. 6, X-ray dose distribution data, which is a piece of the raw data, is generated for each line L1 of the scanogram (the plane image G1) taken in step S2.

Figure 7:
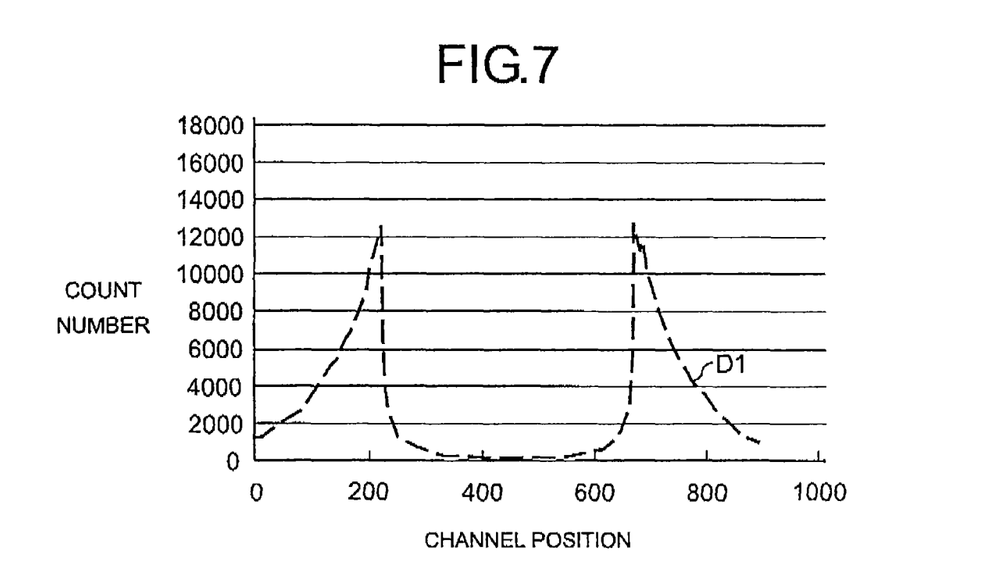
FIG. 7 is a graph showing raw data on the line shown in FIG. 6.

For example, the raw data D1 as shown in FIG. 7, namely the X-ray dose distribution data (the count number distribution data) is generated by: inversely transforming the scanogram data for each line; and returning the pixel scale (for example, 512 pixels) to a channel scale (for example, 90 pixels) of the X-ray detector 3e. In this manner, the raw data D1 is generated from the scanogram by transforming a CT value of each pixel to the X-ray dose (the count number) of each channel seriately from one line to another. Either or both of the plane image G1 and the lateral surface image G2 may be used as the scanogram(s).

Returning to FIG. 3, after the process in step S4, genuine data is generated from the generated raw data (step S5). In step S5, the genuine data is generated by use of: the tube current information acquired in step S3; and scan conditions (for example, the tube voltage, the rotation speed, FOV (effective field of view) and the like).

Figure 8:
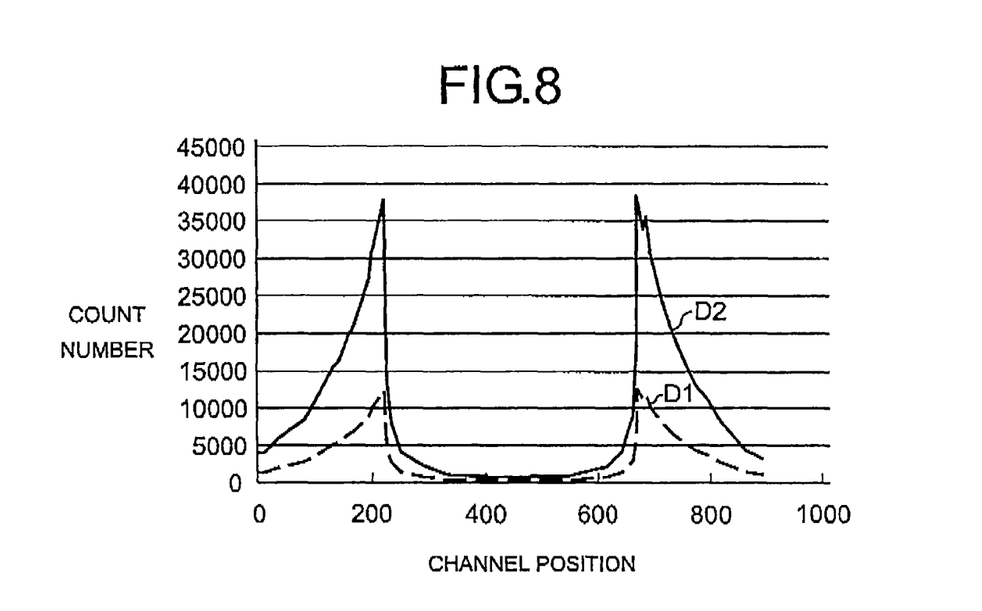
FIG. 8 is a graph showing the raw data on the line shown in FIG. 6 and genuine data corresponding to the raw data.

For example, genuine date D2 is generated by tripling the raw data D1, as shown in FIG. 8. The coefficient for this generation is determined on the basis of the tube current information and the scan conditions so that the genuine data D2 showing the dose distribution of the X-ray, which the X-ray detector 3e actually received when taking the scanograms, can be obtained.

Figure 9:
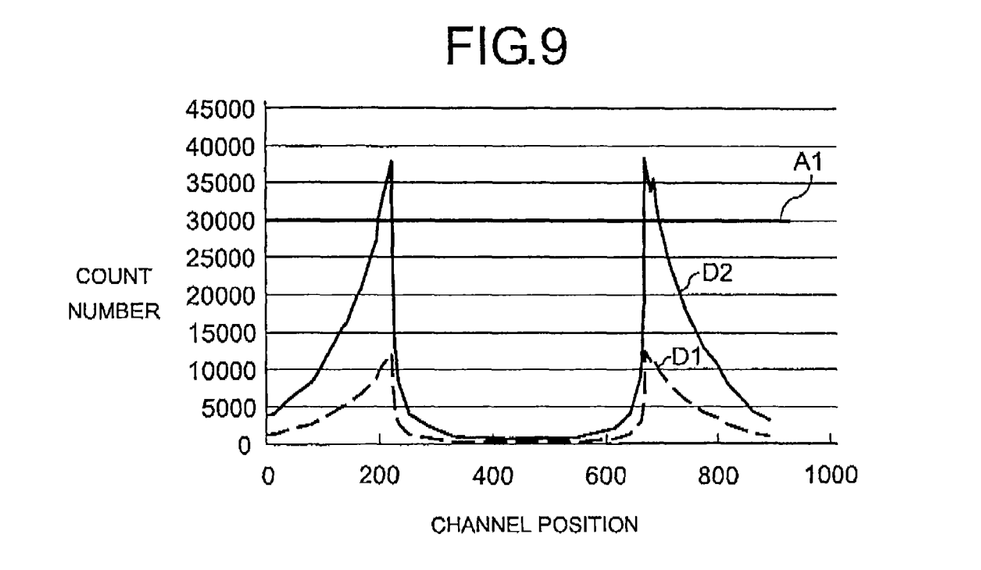
FIG. 9 is a graph for explaining how a threshold value is set for the genuine data.

Returning to FIG. 3, after the process in step S5, a threshold value is set for the genuine data thus generated (step SG). In step S6, a lower limit value A1, above which an overflow artifact (a first artifact) may appear, is set as the threshold value as shown in FIG. 9. In this case, the lower limit value A1 is set, for example, at 30000 which is the maximum value of the count capacity (integration capacity) of the data collector 3f. Although the lower limit value A1 is automatically set from the count capacity of the data collector 3f, how to set the lower limit value A1 is not limited to this. The lower limit value may be set in advance in response to the user's input manipulation on the manipulation unit 4d.

Figure 10:
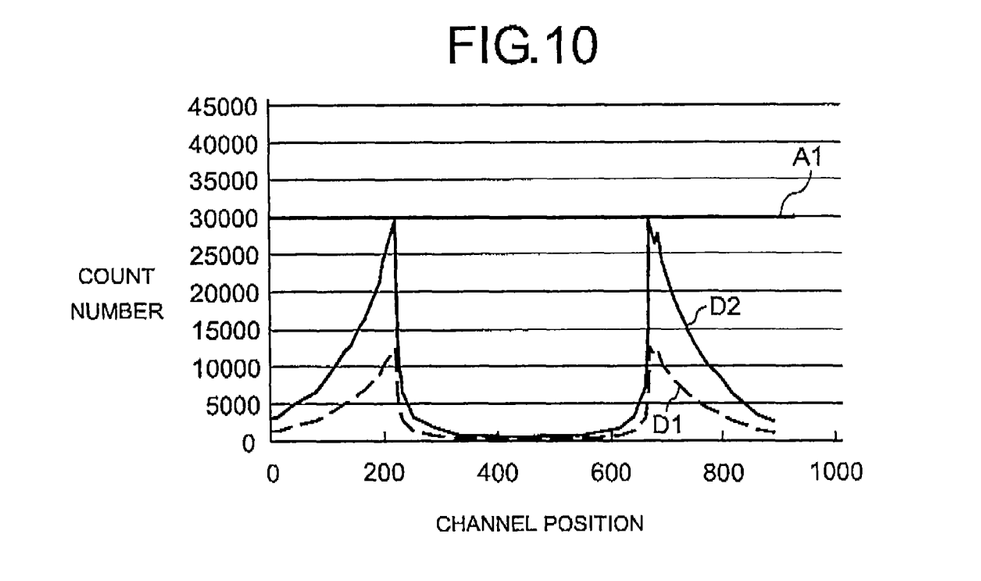
FIG. 10 is a graph for explaining how the tube current is adjusted on the basis of the threshold value.

Returning to FIG. 3, after the process in step S6, the tube current is adjusted on the basis of the X-ray dose (the count number) in the genuine data and the threshold value (step S7). In step S7, when as shown in FIG. 10, the genuine data D2 is changed to make the X-ray dose (the count number) in the genuine data D2 smaller than the lower limit value A1, the tube current is accordingly adjusted. The process of making changes to the genuine data D2 is carried out for each line, as described above.

For example, because the X-ray dose (the count number) in the genuine data D2 generated in step S5 exceeds the lower limit value A1 (see FIG. 9), the coefficient is changed from 3 to 2.5 in step S7 in order to make the X-ray dose in the genuine data D2 smaller than the lower limit value A1 (see FIG. 10). In response to this change, the tube current value is automatically changed as well. For example, at first, since the coefficient is 3, and the tube current value is once set at 300 mA. Once the coefficient is changed from 3 to 2.5, the tube current value is accordingly changed to 250 mA. By this, tomographic images are taken by use of the tube current value thus adjusted. Hence, no overflow artifact occurs, and tomographic images with a better image quality can be obtained.

Figure 11:
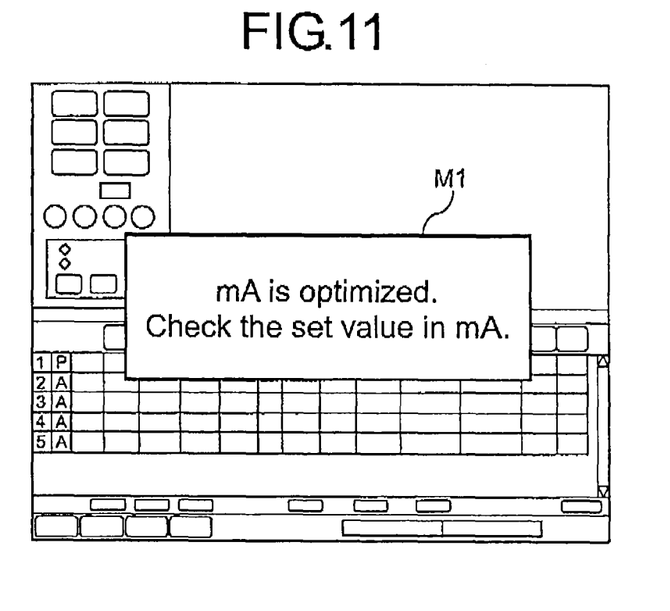
FIG. 11 is a schematic for explaining a message which informs that the tube current is adjusted.

Returning to FIG. 3, after the process in step S7, a message informing that the tube current value is changed is displayed (step S8). In step S8, a message M1 to show a content stating "mA is optimized. Check the set value in mA." is displayed on the display 4e, as shown in FIG. 11. Thereby, the user can become aware that the tube current is optimized through automatic adjustment by seeing the message M1. It should be noted that if the message M1 as described above is displayed after the automatic adjustment, the user may think that the tube current value once set has changed for some unknown reason. In this case, the user would set the tube current value again, or think a trouble occurs in the system.

Figure 12:
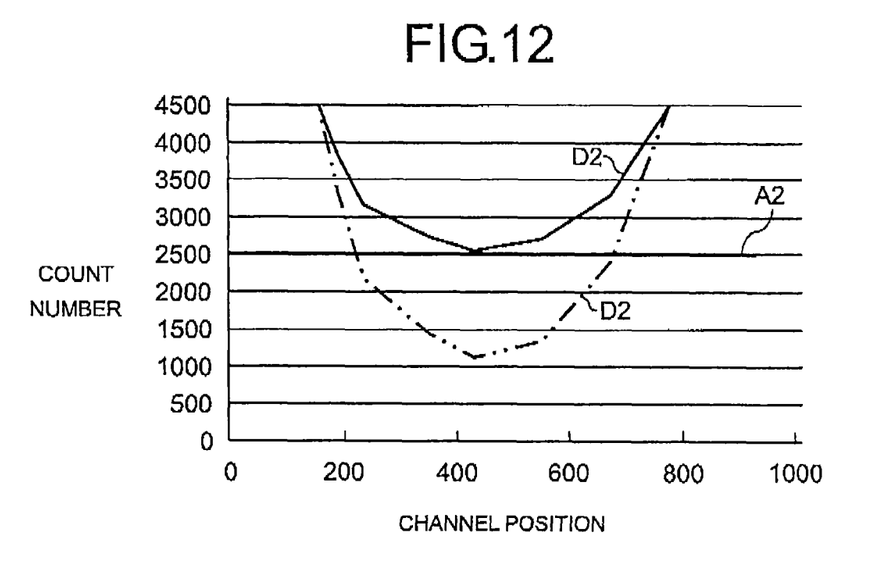
FIG. 12 is a graph for explaining another example of the adjustment of the tube current on the basis of the threshold.

In this respect, in step S6, as shown in FIG. 12, an upper limit value A2, below which another artifact, for example a dark-band artifact (a second artifact), may appear, may be set as the threshold value. This upper limit value A2 is set in advance response to the user's input manipulation on the manipulation unit 4d. In a case where the upper limit value A2, below which the dark-band artifact appears, is set, the genuine data D2 is changed in step S7 in order to make the X-ray dose (the count number) in the genuine data D2 larger than the upper limit value A2 in the way reverse to what has been described (in FIG. 12, the chain double-dashed line represents the genuine data D2 before the change, while the continuous line represents the genuine data D2 after the change).

It should be noted that, in step S6, if either one of the threshold values (the lower limit value A1 and the upper limit value A2) corresponding respectively to the overflow artifact and the dark-band artifact is set, it serves the purpose. This is because the genuine data tends to produce a waveform exclusively representing either one of the overflow artifact and the dark-band artifact.

In addition, in step S7, in a case where the tube current is not intended to be automatically adjusted, that is to say, in a case where the genuine data is not intended to be changed, a warning message to inform that an overflow artifact is likely to appear if the X-ray dose (the count number) in the genuine data is not smaller than the lower limit value A1 (see FIG. 9) may be displayed on the display 4e. This enables the user to become aware that an overflow artifact is likely to appear by seeing the warning message, and to change the tube current.

Furthermore, a warning message to inform that a darkband artifact is likely to appear if the X-ray dose (the count value) in the genuine data is not larger than the upper limit value A2 (see FIG. 12) may be displayed on the display 4e in a case where; in step S6, the upper limit value A2, below which a dark-band artifact appears, is set; and in step S7, the tube current is not intended to be automatically adjusted, that is to say, the genuine data is not intended to be changed. As in the above-described case, this enables the user to become aware that a dark-band artifact is likely to appear by seeing the warning message, and to change the tube current.

As described above, the embodiments generate the genuine data representing the X-ray dose distribution from one of the scanograms (for example, the plane image G1, the lateral surface image G2, and the like), and set the threshold values for the genuine data. In addition, the embodiments adjust the tube current for taking tomographic images of the subject P in accordance with the comparison between the X-ray dose in the generated genuine data and the threshold values. This makes the tube current adjusted within a range where no artifact appears, instead of being adjusted within a limited range of the maximum value and the minimum value determined by the system capacities. Hence, it is possible to suppress the occurrence of artifacts such as overflow artifacts and dark-band artifacts, and thereby to improve the image quality of tomographic images.

Furthermore, since the message to inform that the tube current for taking tomographic images of the subject P is adjusted is displayed, the user can become aware that the tube current is optimized through the automatic change by seeing the message. For example, it is possible to prevent the user from resetting the tube current value, or from thinking that a trouble occurs in the system, while considering that the tube current value once set has changed for some unknown reason.

Moreover, since the lower limit value A1, above which an overflow artifact appears, is set as one of the threshold values, and since the tube current for taking tomographic images of the subject P is adjusted in order to make the X-ray dose in the genuine data smaller than the lower limit value A1, it is possible to suppress the occurrence of the overflow artifact, and accordingly to improve the image quality of the tomographic images securely.

What is more, since the upper limit value A2, below which a dark-band artifact appears, is set as the other of the threshold values, and since the tube current for taking tomographic images of the subject P is adjusted in order to make the X-ray dose in the genuine data larger than the upper limit value A2, it is possible to suppress the occurrence of the dark-band artifact, and accordingly to improve the image quality of the tomographic images securely.

It should be noted that although the foregoing embodiments generate the genuine data from one of the scanograms created by the image processor 4b, the generation of the genuine data is not limited to this. The genuine data may be created directly from the raw data to be produced while the scanograms are being created by the image processor 4b. In this case, since the raw data is stored in the storage 4c while the scanograms are being created, the raw data is used by being retrieved from the storage 4b when the genuine data is generated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic system comprising:
    a tube current setting section for setting a tube current for taking a scanogram of a subject;
    an X-ray tube for radiating an X-ray to the subject on the basis of the tube current for taking the scanogram, the tube current set by the tube current setting section;
    an X-ray detector for detecting the X-ray radiated by the X-ray tube and transmitted through the subject;
    a data collector for collecting X-ray dose distribution data, which shows the dose distribution of the X-ray detected by the X-ray detector;
    an image processor for creating the scanogram from the X-ray dose distribution data collected by the data collector;
    a genuine data generator for generating genuine data showing the dose distribution of the X-ray detected by the X-ray detector, from the scanogram created by the image processor, or from raw data produced in a process of creating the scanogram by the image processor;
    a threshold value setting section for setting a threshold value for the genuine data generated by the genuine data generator; and
    a tube current adjustor for adjusting a tube current for taking a tomographic image of the subject in accordance with a comparison between the X-ray dose in the genuine data generated by the genuine data generator and the threshold value set by the threshold value setting section.

2. The X-ray diagnostic system according to claim 1, further comprising a display for displaying a message to inform that the tube current for taking the tomographic image of the subject is adjusted by the tube current adjustor.

3. The X-ray diagnostic system according to claim 1, wherein
    the threshold value setting section sets a lower limit value, above which an artifact appears, as the threshold value, and
    the tube current adjustor adjusts the tube current for taking the tomographic image of the subject in a way that the X-ray dose in the genuine data generated by the genuine data generator is made smaller than the lower limit value set by the threshold value setting section.

4. The X-ray diagnostic system according to claim 2, wherein
    the threshold value setting section sets a lower limit value, above which an artifact appears, as the threshold value, and
    the tube current adjustor adjusts the tube current for taking the tomographic image of the subject in a way that the X-ray dose in the genuine data generated by the genuine data generator is made smaller than the lower limit value set by the threshold value setting section.

5. The X-ray diagnostic system according to claim 1, wherein
    the threshold value setting section sets an upper limit value, below which an artifact appears, as the threshold value, and
    the tube current adjustor adjusts the tube current for taking the tomographic image of the subject in a way that the X-ray dose in the genuine data generated by the genuine data generator is made larger than the upper limit value set by the threshold value setting section.

6. The X-ray diagnostic system according to claim 2, wherein
    the threshold value setting section sets an upper limit value, below which an artifact appears, as the threshold value, and
    the tube current adjustor adjusts the tube current for taking the tomographic image of the subject in a way that the X-ray dose in the genuine data generated by the genuine data generator is made larger than the upper limit value set by the threshold value setting section.

7. The X-ray diagnostic system according to claim 1, wherein
    the threshold value setting section sets a lower limit value above which a first artifact appears, and an upper limit value below which a second artifact appears, as the threshold value, and
    the tube current adjustor adjusts the tube current for taking the tomographic image of the subject in a way that the X-ray dose in the genuine data generated by the genuine data generator is made smaller than the lower limit value set by the threshold value setting section, or larger than the upper limit value set by the threshold value setting section.

8. The X-ray diagnostic system according to claim 2, wherein
    the threshold value setting section sets a lower limit value above which a first artifact appears, and an upper limit value below which a second artifact appears, as the threshold value, and
    the tube current adjustor adjusts the tube current for taking the tomographic image of the subject in a way that the X-ray dose in the genuine data generated by the genuine data generator is made smaller than the lower limit value set by the threshold value setting section, or larger than the upper limit value set by the threshold value setting section.

9. An X-ray diagnostic method comprising the steps of:
    setting a tube current for taking a scanogram of a subject;
    radiating an X-ray to the subject on the basis of the set tube current for taking the scanogram;
    detecting the X-ray transmitted through the subject;

collecting X-ray dose distribution data, which shows the dose distribution of the detected X-ray;

creating the scanogram from the collected X-ray dose distribution data;

generating genuine data showing the dose distribution of the X-ray from the created scanogram, or from raw data produced in a process of creating the scanogram;

setting a threshold value for the generated genuine data; and adjusting a tube current for taking a tomographic image of the subject in accordance with a comparison between the X-ray dose in the generated genuine data and the set threshold value.

10. The X-ray diagnostic method according to claim 9, further comprising the step of displaying a message to inform that the tube current for taking the tomographic image of the subject is adjusted.

11. The X-ray diagnostic method according to claim 9, wherein in the threshold value setting step, a lower limit value, above which an artifact appears, is set as the threshold value, and in the tube current adjusting step, the tube current for taking the tomographic image of the subject is adjusted in a way that the X-ray dose in the generated genuine data is made smaller than the set lower limit value.

12. The X-ray diagnostic method according to claim 10, wherein in the threshold value setting step, a lower limit value, above which an artifact appears, is set as the threshold value, and in the tube current adjusting step, the tube current for taking the tomographic image of the subject is adjusted in a way that the X-ray dose in the generated genuine data is made smaller than the set lower limit value.

13. The X-ray diagnostic system according to claim 9, wherein in the threshold value setting step, an upper limit value, below which an artifact appears, is set as the threshold value, and in the tube current adjusting step, the tube current for taking the tomographic image of the subject is adjusted in a way that the X-ray dose in the generated genuine data is made larger than the set upper limit value.

14. The X-ray diagnostic system according to claim 10, wherein in the threshold value setting step, an upper limit value, below which an artifact appears, is set as the threshold value, and in the tube current adjusting step, the tube current for taking the tomographic image of the subject is adjusted in a way that the X-ray dose in the generated genuine data is made larger than the set upper limit value.

15. The X-ray diagnostic system according to claim 9, wherein in the threshold value setting step, a lower limit value above which a first artifact appears, and an upper limit value below which a second artifact appears, are set as the threshold value, and in the tube current adjusting step, the tube current for taking the tomographic image of the subject is adjusted in a way that the X-ray dose in the generated genuine data is made smaller than the set lower limit value, or larger than the set upper limit value.

16. The X-ray diagnostic system according to claim 10, wherein in the threshold value setting step, a lower limit value above which a first artifact appears, and an upper limit value below which a second artifact appears, are set as the threshold value, and in the tube current adjusting step, the tube current for taking the tomographic image of the subject is adjusted in a way that the X-ray dose in the generated genuine data is made smaller than the set lower limit value, or larger than the set upper limit value.

\* \* \* \* \*